US012757864B2

(12) United States Patent
Sims

(10) Patent No.: US 12,757,864 B2
(45) Date of Patent: Oct. 13, 2026

(54) ODOR ADSORBING PET PAD WITH A BIO-ENZYMATIC ODOR REDUCER

(71) Applicant: BEYOND ENVIRONMENTAL, LLC., Geneva, IL (US)

(72) Inventor: Bryan Sims, Geneva, IL (US)

(73) Assignee: BEYOND ENVIRONMENTAL, LLC., Geneva, IL (US)

( * ) Notice: Subject to any disclaimer, the term of this patent is extended or adjusted under 35 U.S.C. 154(b) by 245 days.

(21) Appl. No.: 18/507,802

(22) Filed: Nov. 13, 2023

(65) Prior Publication Data

US 2024/0156048 A1 May 16, 2024

Related U.S. Application Data

(60) Provisional application No. 63/384,033, filed on Nov. 16, 2022.

(51) Int. Cl.

*A01K 1/015* (2006.01)
*A61L 11/00* (2006.01)
*C12N 1/20* (2026.01)

(52) U.S. Cl.

CPC ............ *A01K 1/0157* (2013.01); *A61L 11/00* (2013.01); *C12N 1/20* (2013.01)

(58) Field of Classification Search

CPC ........................................................ C12N 1/07

See application file for complete search history.

(56) References Cited

U.S. PATENT DOCUMENTS

| | | | |
|---|---|---|---|
| 4,165,281 | A | 8/1979 | Kuriyama et al. |
| 4,826,497 | A | 5/1989 | Marcus et al. |
| 4,913,954 | A | 4/1990 | Mack |
| 5,580,770 | A | 12/1996 | Defilippi |
| 5,819,688 | A | 10/1998 | Walker |
| 6,405,676 | B1 | 6/2002 | Mochizuki |
| 7,874,266 | B2 | 1/2011 | Axelrod |
| 8,101,532 | B1 | 1/2012 | Yananton |
| 8,945,905 | B2 | 2/2015 | Brandt et al. |
| 2007/0065397 | A1 | 3/2007 | Ito et al. |
| 2015/0334984 | A1 | 11/2015 | Ruesswick |

FOREIGN PATENT DOCUMENTS

| | | | |
|---|---|---|---|
| BE | 1018722 | A5 | 7/2011 |
| CN | 205756284 | U | 12/2016 |
| CN | 104126515 | B | 1/2017 |
| CN | 112136698 | A | 12/2020 |
| JP | 2013208432 | A | 10/2013 |
| JP | 6148912 | B2 | 6/2017 |
| KR | 20200021812 | A | 3/2020 |
| KR | 20200043694 | A | 4/2020 |

OTHER PUBLICATIONS

Search Report and Opinion received in European Application No. 23210173.3, dated Mar. 20, 2024.

*Primary Examiner* — Arti Singh-Pandey

(74) *Attorney, Agent, or Firm* — Greer, Burns & Crain, Ltd

(57) ABSTRACT

An odor adsorbing pet pad includes an adsorbent mat with a nonwoven hydrophobic fabric; and a bio-enzymatic odor reducer with bacillus in spore form which is applied to the adsorbent mat. In particular, the bacillus in the bio-enzymatic odor reducer is activated when animal waste interacts with the adsorbent mat of the odor adsorbing pet pad.

16 Claims, 3 Drawing Sheets

ODOR ADSORBING PET PAD WITH A BIO-ENZYMATIC ODOR REDUCER

RELATED APPLICATION

This application is a Non-Provisional of, and claims 35 U.S.C. 119 priority from, U.S. Patent Application No. 63/384,033 filed Nov. 16, 2022, the entire contents of which are incorporated by reference herein.

BACKGROUND

The present disclosure relates generally to odor reducing pads for pets, and more specifically to odor adsorbing pet pads with a bio-enzymatic odor reducer.

A common issue for pet owners, especially those who have domesticated dogs, is the need to frequently take their pets outside so that they may urinate and/or defecate. This issue is especially relevant for pet owners who live in urban areas or cold weather environments. Additionally, pet owners who spend a large portion of the day away from their home are not always able to take their pets outside when they need to urinate and/or defecate.

As a result, there have been attempts to create pads, often called piddle pads, that reduce the odor caused by pets urinating and/or defecating inside a home. Conventional piddle pads include absorbent materials, which have fibers or chemicals that absorb a high level of liquid and hold the liquid within their cell structures. However, piddle pads that use absorbent materials have significant downsides.

Piddle pads with absorbent material typically have to be replaced well before they become full of animal waste because they fail to effectively reduce the odor of the animal waste. Specifically, the absorbent material in typical piddle pads locks the odor causing proteins in their cellular structures. Thereafter, the odor causing proteins decompose, causing odor. Additionally, piddle pads with absorbent material must be washed frequently, usually once daily.

Certain piddle pads use adsorbent materials, where the animal waste is held by the fibers of the adsorbent materials. However, existing piddle pads which use adsorbent materials typically are unable to effectively reduce the odor emitted by the animal waste. In particular, the chemical compounds or micronutrients used in conjunction with the existing piddle pads that use adsorbent material do not sufficiently reduce the odor causing proteins in the animal waste. Therefore, existing piddle pads fail to sufficiently reduce the odor caused by animal waste, must be changed regularly, and are generally inconvenient to use. As such, there is the need for an improved piddle pad that effectively reduces the odor of animal waste, is convenient to use, and does not to be replaced regularly.

SUMMARY

The above-listed need is met or exceeded by the present odor adsorbing pet pads with a bio-enzymatic odor reducer. An important feature of the present disclosure is the use of an adsorbent mat which keeps the liquid portion of animal waste open to atmosphere, so that the liquid evaporates as opposed to being retained within the mat. A downside to conventional piddle pads is that they prevent the liquids of the animal waste from evaporating, which results in the odor being retained by the piddle pad. In contrast, the present odor adsorbing pet pad does not retain the liquid of the animal waste, but allows the liquid to evaporate and more effectively react with the bio-enzymatic odor reducer.

Accordingly, another important feature of the present disclosure is the bio-enzymatic odor reducer which consumes the odor-causing proteins of the animal waste. In particular, the bacillus within the bio-enzymatic odor reducer is provided in spore form. Further, the bacillus spores are activated when they interact with the liquid of the animal waste. Additionally, the bacillus spores become dormant after consuming the animal waste. Moreover, the bio-enzymatic odor reducer is optionally provided in liquid form, so that it is conveniently applied to the adsorbent mat. In this way, the user is able to wash the odor adsorbing pet pad, and simply reapply the bio-enzymatic odor reducer. Therefore, the presently disclosed odor adsorbing pet pad is reusable, thereby decreasing the effort and expense associated with reducing the odor caused by animal waste.

As mentioned above, a significant feature of the present disclosure is the ability to reuse the odor adsorbing pet pad by reapplying the bio-enzymatic odor reducer. Reapplying the bio-enzymatic odor reducer is preferably accomplished by spraying the odor reducer onto the adsorbent mat and allowing it to dry. By washing the odor adsorbing pet pad, and reapplying the bio-enzymatic odor reducer, the odor adsorbing pet pad has a much longer functional life than currently available piddle pads, which are disposable. Additionally, the simple application of the bio-enzymatic odor reducer makes the presently disclosed odor adsorbing pet pad more convenient than currently available piddle pads.

Further, the user optionally adds additional bio-enzymatic odor reducer to the adsorbent mat as desired. This is especially the case when a pet urinates and/or defecates on a particular spot on the odor adsorbing pet pad, and additional bio-enzymatic odor reducer is needed on that spot.

More specifically, an embodiment of the present disclosure is an odor adsorbing pet pad which includes an adsorbent mat with a nonwoven hydrophobic fabric, and a bio-enzymatic odor reducer which includes bacillus in spore form. The bacillus is applied to the adsorbent mat and is activated when animal waste interacts with the adsorbent mat. In a preferred embodiment, the adsorbent mat also includes a waterproof backing beneath the nonwoven hydrophobic fabric of the adsorbent mat. Preferably still, the waterproof backing includes polyethylene or any suitable waterproof plastic.

In another embodiment, the bacillus is one or more of *B. angloliquefaciens, B. licheniformis, B. subtilis* and *B. pumilus*. In yet another embodiment, the adsorbent mat includes a needle punch polyester and polypropylene blend and has a weight between approximately 250 grams per square meter (gsm) and approximately 700 gsm.

Preferably, the bio-enzymatic odor reducer also includes at least one odor counteractant and/or an emulsifier. Preferably still, the bio-enzymatic odor reducer has approximately 20,000,000 colony forming units (CFU) of the bacillus per square inch of the adsorbent mat. In a preferred embodiment, the odor adsorbing pet pad is machine washable.

A second embodiment of the present disclosure is a method of use for an odor adsorbing pet pad, the method including the steps of providing an adsorbent mat and applying a bio-enzymatic odor reducer with bacillus in spore form to the adsorbent mat. Importantly, the bacillus is activated when animal waste interacts with the adsorbent mat. In a preferred embodiment, the method of use also includes washing the adsorbent mat and reapplying the bio-enzymatic odor reducer to the adsorbent mat after washing the adsorbent mat.

In another preferred embodiment, the step of washing the adsorbent mat includes using a strong bleach solution and soap. Preferably, the step of applying the bio-enzymatic odor reducer includes soaking the adsorbent mat in the bio-enzymatic odor reducer and allowing the adsorbent mat to dry.

DETAILED DESCRIPTION

Figure 1:
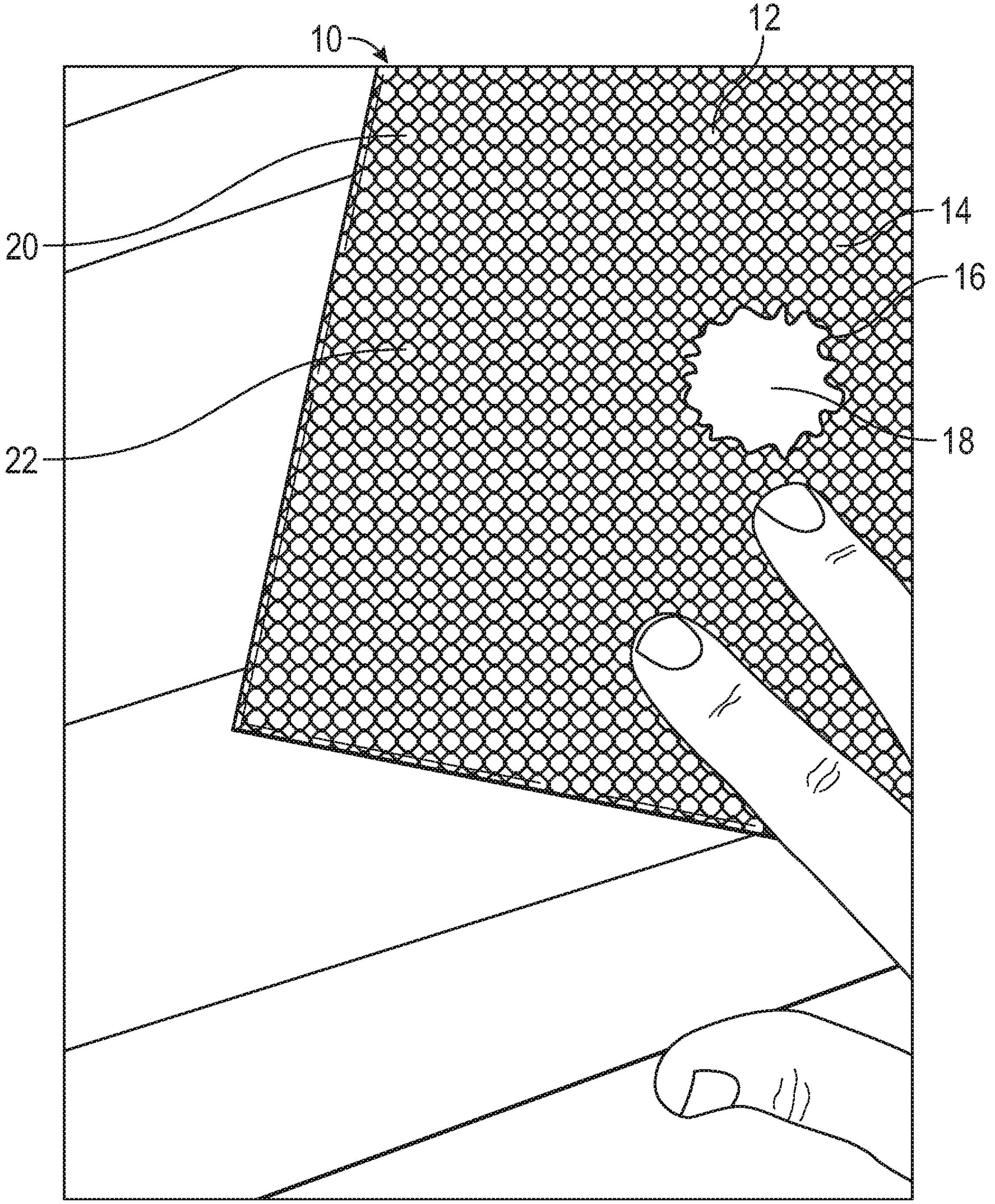
FIG. 1 is a fragmentary top plan view of an odor adsorbing pet pad with a bio-enzymatic odor reducer.
Figure 2:
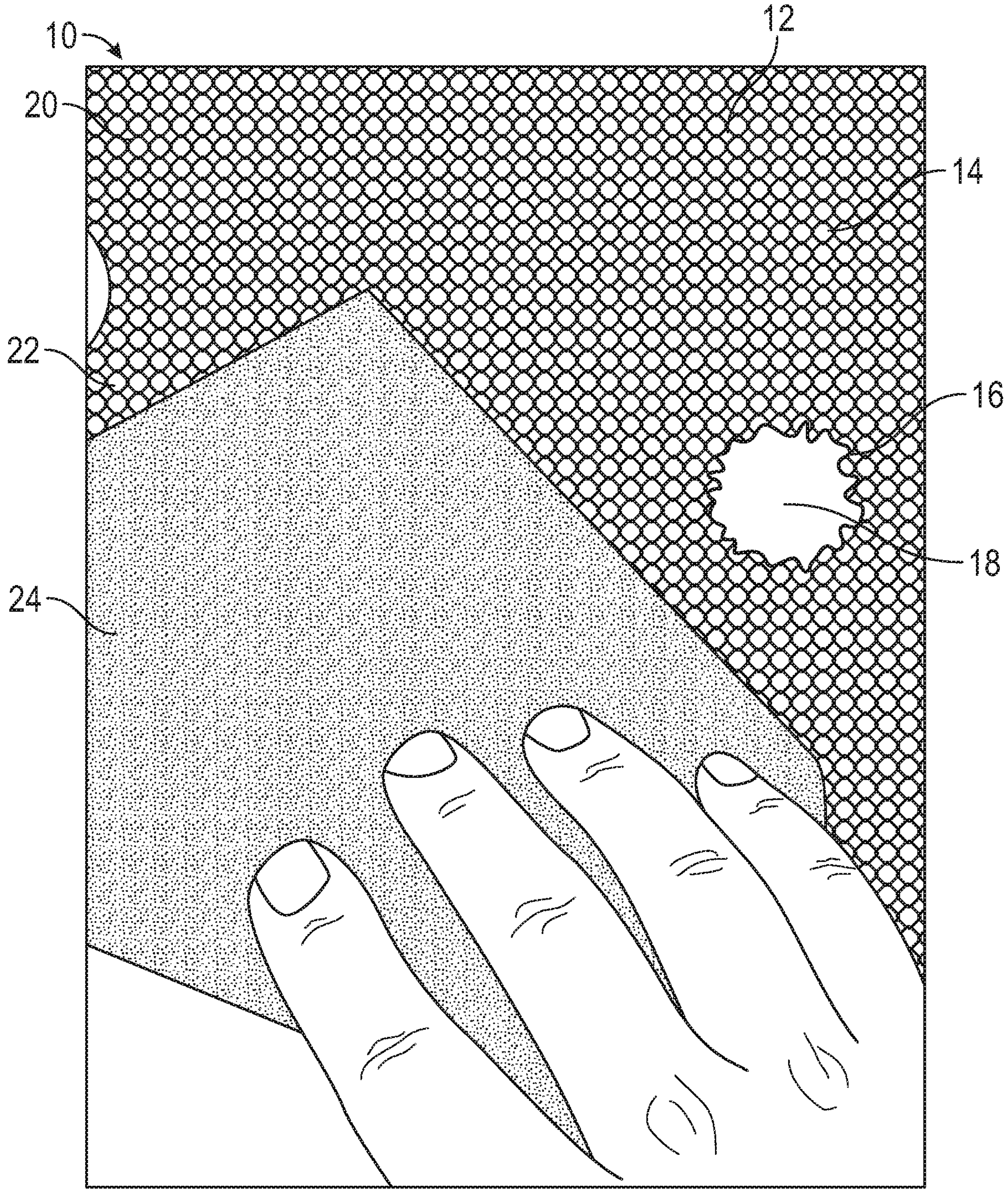
FIG. 2 is a fragmentary top plan view of the odor adsorbing pet pad of FIG. 1.
Figure 3:
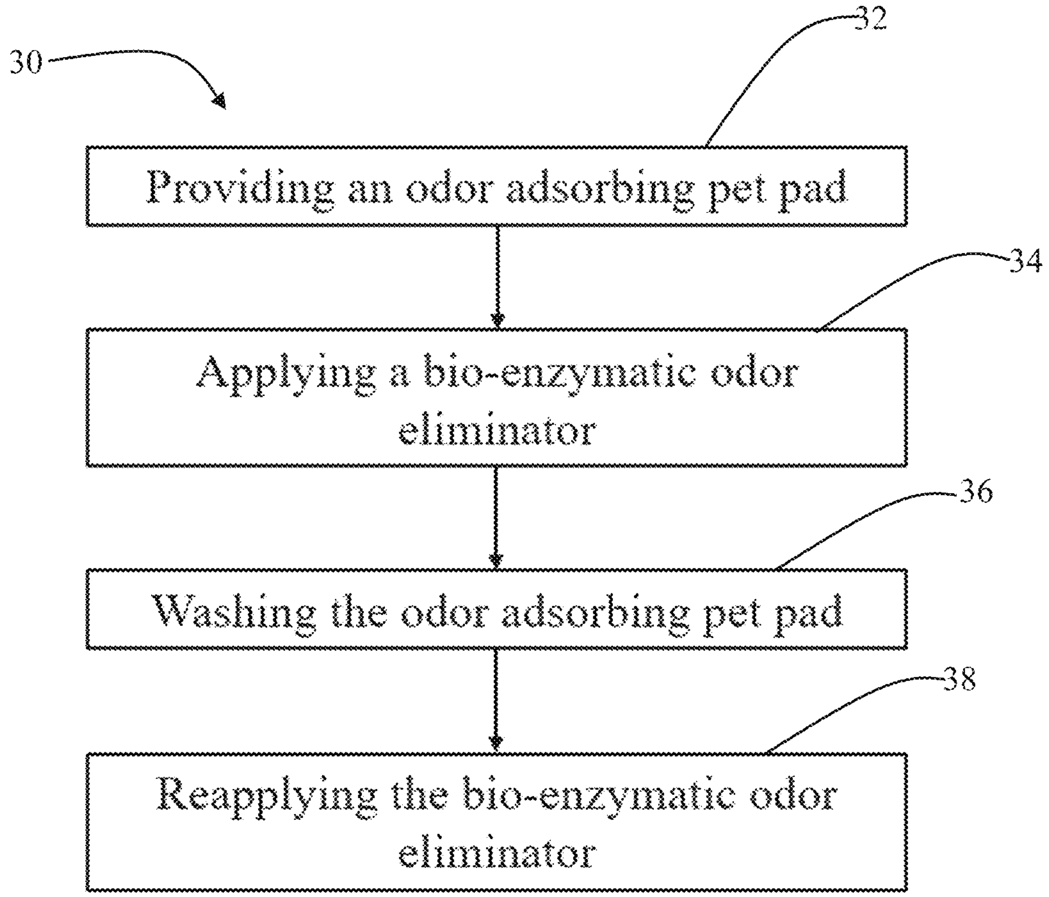
FIG. 3 is a flow chart depicting a method of use for the odor adsorbing pet pad of FIG. 1.

Referring now to FIGS. 1 and 2, the present odor adsorbing pet pad with a bio-enzymatic odor reducer is generally designated 10, and includes an adsorbent mat 12 made of a non-woven hydrophobic fabric 14. A bio-enzymatic odor reducer 16, which includes bacillus 18, is applied to the adsorbent mat 12. It is preferred that the bacillus 18 is provided in spore form. Additionally, the bacillus 18 in the bio-enzymatic odor reducer 16 is activated when the adsorbent mat 12 interacts with animal waste (not shown). Accordingly, when a pet (not shown) either urinates and/or defecates on the odor adsorbing pet pad 10, the bacillus 18 transitions from a dormant state to an active state and consumes the animal waste. After the animal waste has been completely consumed, the bacillus 18 returns to its dormant state. In particular, the present inventors surprisingly found that the bacillus 18, when used in conjunction with the adsorbent mat 12, effectively consumes the odor causing proteins that are present in animal waste.

While there are many different species of bacillus 18 which are appropriate for the bio-enzymatic odor reducer 16, it is preferred that the bacillus 18 is *B. angloliquefaciens, B. licheniformis, B. subtilis, B. pumilus*, or a combination thereof. Moreover, the bio-enzymatic odor reducer 16 optionally includes at least one odor counteractant 20 and/or an emulsifier 22. The odor counteractant 20 reduces the odor of the animal waste while the bacillus 18 in the bio-enzymatic odor reducer 16 consumes the odor causing proteins in the animal waste. Further, the emulsifier 22 is optionally included to bind the ingredients of the bio-enzymatic odor reducer 16. It is preferred that the emulsifier 22 is a bio-surfactant, but other emulsifiers are contemplated as are known in the art.

An important feature of the present disclosure is the amount of bacillus 18 which is present in the bio-enzymatic odor reducer 16. Specifically, the bacillus 18 is preferably provided in spore form, and the amount of bacillus 18 present depends on the number of colony forming units (CFU) applied to the adsorbent mat 12. In particular, the preferred concentration of bacillus 18 present on the adsorbent mat 12 is approximately 20,000,000 CFU per square inch of the adsorbent mat 12. However, it is understood that there exists a wide range of potential CFU per square inch of the bacillus 18 present on the adsorbent mat 12 which are appropriate for the present odor adsorbing pet pad 10, and the concentration may vary to suit the application.

Additionally, the non-woven hydrophobic fabric 14 of the adsorbent mat 12 is preferably made of a needle punch polyester and polypropylene blend. However, it is understood that any non-woven hydrophobic fabric 14 is appropriate for use in the adsorbent mat 12. Importantly, the non-woven hydrophobic fabric 14 keeps the liquid portion of the animal waste open to the atmosphere. As a result, the liquid portion of the animal waste evaporates, thereby improving the usable life of the odor adsorbing pet pad 10. Additionally, the bacillus 18 effectively consumes the odor causing proteins in the animal waste when used with the adsorbent mat 12.

It is preferred that the density of the nonwoven hydrophobic fabric 14 is between approximately 250 grams per square meter (gsm) and approximately 700 gsm. The density of the nonwoven hydrophobic fabric 14 is adjustable depending on the preferred fabric used in the adsorbent mat 12 as is known in the art.

Optionally included is a waterproof backing 24 beneath the nonwoven hydrophobic fabric 14 of the adsorbent mat 12. In particular, the waterproof backing 24 is optionally provided so that the animal waste does not seep through the adsorbent mat 12. Moreover, the waterproof backing 24 improves the durability of the odor adsorbing pet pad 10. While it is preferred that the waterproof backing 24 include polyethylene, it is understood that any durable and hydrophobic material is appropriate for use as the waterproof backing 24.

Another important feature of the present odor adsorbing pet pad 10 is the fact that it is reusable. In particular, the odor adsorbing pet pad 10 is machine washable. Importantly, including the waterproof backing 24 extends the usable life of the adsorbent mat 12, especially when the odor adsorbing pet pad 10 is washed frequently. Moreover, it is preferred that the odor adsorbing pet pad 10 is washed using a strong bleach solution and soap, to remove the previously applied bio-enzymatic odor reducer 16 before reapplying a fresh coat of the bio-enzymatic odor reducer 16.

Another important feature of the present disclosure is a method of use 30 for the odor adsorbing pet pad 10. In particular, the method 30 includes a step 32 of providing the adsorbent mat 12, and a step 34 of applying the bio-enzymatic odor reducer 16, which includes bacillus 18 in spore form, to the adsorbent mat 12. In a preferred embodiment, the bio-enzymatic odor reducer 16 is applied to the adsorbent mat 12 by soaking the adsorbent mat 12 in the bio-enzymatic odor reducer 16 and allowing the adsorbent mat 12 to dry. Spraying the bio-enzymatic odor reducer 16 on the adsorbent mat 12 is also contemplated. Other methods for applying the bio-enzymatic odor reducer 16 to the adsorbent mat 12 are contemplated as is known in the art.

Additionally, the method of use 30 optionally includes a step 36 of washing the adsorbent mat 12. It is preferred that the step 36 of washing the adsorbent mat 12 is carried out by machine washing with a strong bleach solution and soap. However, any suitable method for washing the adsorbent mat 12, and removing the previously applied bio-enzymatic odor reducer 16, is contemplated as is known in the art. Finally, the method of use 30 optionally includes a step 38 of reapplying the bio-enzymatic odor reducer 16 to the adsorbent mat 12 after the step 36 of washing the adsorbent mat 12. In this way, the present odor adsorbing pet pad 10 is reusable, thereby decreasing the cost and difficulty in reducing the odor caused by animal waste.

It is also contemplated that the step 38 of reapplying the bio-enzymatic odor reducer 16 is optionally performed without the step 36 of washing the odor adsorbing pet pad 36. In particular, a user of the odor adsorbing pet pad 10 optionally applies additional bio-enzymatic odor reducer 16 without washing the adsorbent mat 12. This is particularly the case when a large amount of animal waste is applied to the odor adsorbing pet pad 10. Alternatively, if the pet urinates and/or defecates in a particular spot of the odor adsorbing pet pad 10, the pet owner optionally applies additional bio-enzymatic odor reducer 16 to that spot.

While a particular embodiment of the present odor adsorbing pet pad has been described herein, it will be appreciated by those skilled in the art that changes and modifications may be made thereto without departing from the invention in its broader aspects and as set forth in the following claims.

The invention claimed is:

1. A machine washable odor adsorbing pet pad comprising: an adsorbent mat comprising a nonwoven hydrophobic fabric; and a bio-enzymatic odor reducer comprising bacillus in spore form, said bio-enzymatic odor reducer being applied to said adsorbent mat, such that said bacillus is activated when liquid animal waste interacts with said adsorbent mat, and said bacillus become dormant after consuming the animal waste.

2. The machine washable odor adsorbing pet pad of claim 1, wherein said adsorbent mat further comprises a waterproof backing beneath said nonwoven hydrophobic fabric.

3. The machine washable odor adsorbing pet pad of claim 2, wherein said waterproof backing comprises polyethylene.

4. The machine washable odor adsorbing pet pad of claim 1, wherein said bacillus comprises one or more of *B. amyloliquefaciens, B. licheniformis, B. subtilis* and *B. pumilus*.

5. The machine washable odor adsorbing pet pad of claim 1, wherein said adsorbent mat comprises a needle punch polyester and polypropylene blend.

6. The machine washable odor adsorbing pet pad of claim 1, wherein said nonwoven hydrophobic fabric has a density between approximately 250 grams per square meter (gsm) and approximately 700 gsm.

7. The machine washable odor adsorbing pet pad of claim 1, wherein said bio-enzymatic odor reducer further comprises at least one odor counteractant and an emulsifier.

8. The machine washable odor adsorbing pet pad of claim 1, wherein said bio-enzymatic odor reducer comprises approximately 20,000,000 colony forming units (CFU) of said bacillus per square inch.

9. A method of use for a machine washable odor adsorbing pet pad, comprising: providing an adsorbent mat; and applying a bio-enzymatic odor reducer comprising a liquid having bacillus in spore form to said adsorbent mat, such that said bacillus is activated when liquid animal waste interacts with said adsorbent mat, and said bacillus become dormant after consuming the animal waste; wherein said bacillus comprises one or more of *B. amyloliquefaciens, B. licheniformis, B. subtilis* and *B. pumilus*; and wherein said bio-enzymatic odor reducer comprises approximately 20,000,000 colony forming units (CFU) per square inch.

10. The method of claim 9, further comprising reapplying said bio-enzymatic odor reducer to said adsorbent mat after washing said adsorbent mat.

11. The method of claim 9, wherein said step of washing said adsorbent mat includes using a strong bleach solution and soap.

12. The method of claim 9, wherein said adsorbent mat further comprises a waterproof backing beneath said nonwoven hydrophobic fabric.

13. The method of claim 12, wherein said waterproof backing comprises polyethylene.

14. The method of claim 9, wherein said adsorbent mat comprises a needle punch polyester and polypropylene blend.

15. The method of claim 9, wherein said bio-enzymatic odor reducer further comprises at least one odor counteractant and an emulsifier.

16. The method of claim 9, wherein said step of applying said bio-enzymatic odor reducer comprises soaking said adsorbent mat in said bio-enzymatic odor reducer and allowing said adsorbent mat to dry.

* * * * *